(12) United States Patent
Holloway

(10) Patent No.: US 11,090,459 B2
(45) Date of Patent: Aug. 17, 2021

(54) METHODS AND DEVICES FOR APPLYING DYNAMIC, NON-LINEAR OSCILLATIONS AND VIBRATIONS

(71) Applicant: SOLACE LIFESCIENCES, INC., Wilmington, DE (US)

(72) Inventor: G. Blake Holloway, Kerrville, TX (US)

(73) Assignee: Solace Lifesciences, Inc., Wilmington, DE (US)

( * ) Notice: Subject to any disclaimer, the term of this patent is extended or adjusted under 35 U.S.C. 154(b) by 290 days.

(21) Appl. No.: 16/339,962

(22) PCT Filed: Oct. 10, 2017

(86) PCT No.: PCT/US2017/055913
§ 371 (c)(1),
(2) Date: Apr. 5, 2019

(87) PCT Pub. No.: WO2018/068050
PCT Pub. Date: Apr. 12, 2018

(65) Prior Publication Data
US 2019/0282779 A1    Sep. 19, 2019

Related U.S. Application Data

(60) Provisional application No. 62/405,805, filed on Oct. 7, 2016.

(51) Int. Cl.
*A61M 21/02* (2006.01)
*A61M 21/00* (2006.01)

(52) U.S. Cl.
CPC ...... *A61M 21/02* (2013.01); *A61M 2021/0016* (2013.01); *A61M 2021/0022* (2013.01); *A61M 2021/0027* (2013.01); *A61M 2021/0044* (2013.01); *A61M 2021/0072* (2013.01); *A61M 2230/005* (2013.01); *A61M 2230/10* (2013.01)

(58) Field of Classification Search
CPC .......... A61M 21/02; A61M 2021/0016; A61M 2021/0022; A61M 2021/0027; A61M 2021/0044; A61M 2021/0072; A61M 2230/005; A61M 2230/10
See application file for complete search history.

(56) References Cited

U.S. PATENT DOCUMENTS

| | | | |
|---|---|---|---|
| 5,036,858 | A | 8/1991 | Carter et al. |
| 7,769,439 | B2 | 8/2010 | Vesely et al. |
| 2013/0177883 | A1 | 7/2013 | Barnehama et al. |
| 2014/0343354 | A1 | 11/2014 | Larson et al. |
| 2015/0038776 | A1 | 2/2015 | Donnet et al. |
| 2015/0071448 | A1 | 3/2015 | Mesfin |

OTHER PUBLICATIONS

PCT Search Report & Written Opinion dated Feb. 8, 2018 for PCT/US2017/055913 in the name of Solace Lifesciences, Inc. filed on Oct. 10, 2017 (9 pages).

*Primary Examiner* — Kaylee R Wilson
(74) *Attorney, Agent, or Firm* — Fish IP Law, LLP

(57) ABSTRACT

Systems and methods for applying binaural beats to a person are disclosed in a way to prevent the listener from becoming acclimatized to the binaural beats. The system administers varying binaural beat frequencies according to varying progressions of binaural beats from a base binaural beat to a target binaural beat in an irregular manner.

19 Claims, 3 Drawing Sheets

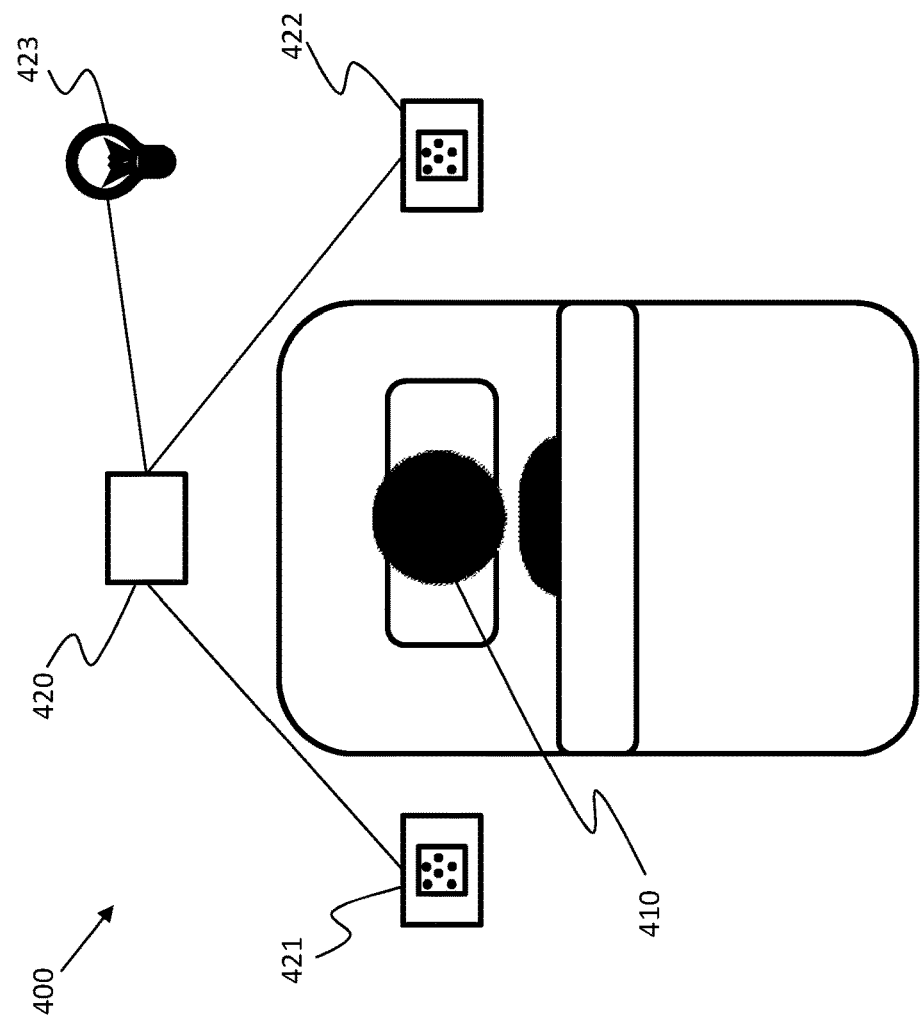
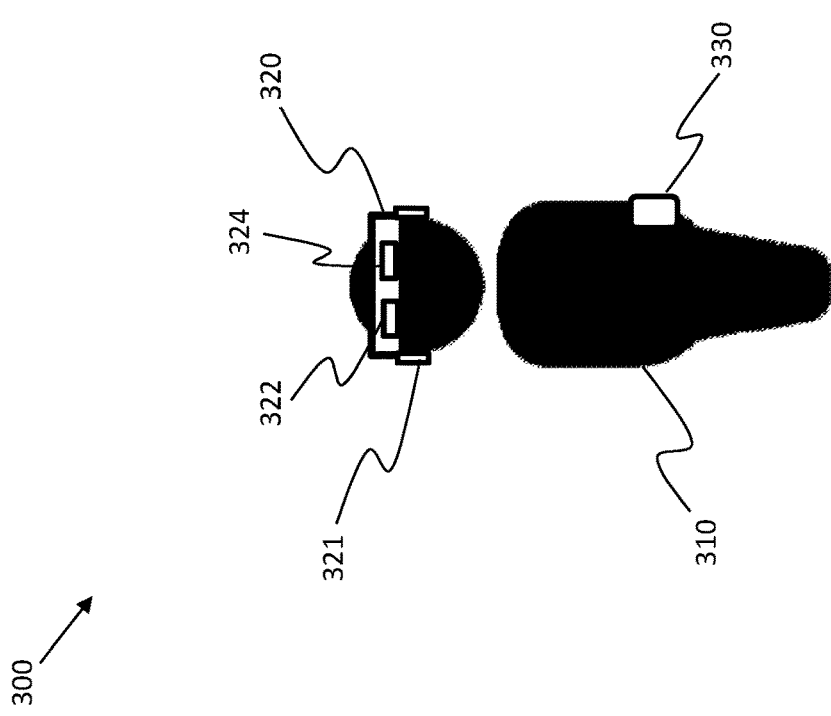

METHODS AND DEVICES FOR APPLYING DYNAMIC, NON-LINEAR OSCILLATIONS AND VIBRATIONS

This application claims the benefit of priority to PCT/US2017/055913, filed on Oct. 10, 2017, which claims the benefit of priority to U.S. provisional application No. 62/405,805, filed on Oct. 7, 2016. This and all other extrinsic references referenced herein are incorporated by reference in their entirety.

FIELD OF THE INVENTION

The field of the invention is brainwave training using binaural beats.

BACKGROUND

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Binaural beats have been used in to entrain brainwaves and induce associated with frequencies of the applied binaural beats.

Table 1 below provides a summary of human brainwave frequencies and the mental state associated with those frequencies.

TABLE 1

Mental States Associated With Brainwave Frequencies In The Prior Art

| Frequency Range | Name | Associated mental state |
| --- | --- | --- |
| <4 Hz | Delta waves | Deep, dreamless sleep, loss of body awareness |
| 4-7 Hz | Theta waves | Deep meditation, relaxation, NREM sleep |
| 7-13 Hz | Alpha waves | Waking relaxation, pre-sleep and pre-wake drowsiness, REM sleep, dreaming |
| 13-39 Hz | Beta waves | Active, busy, or anxious thinking, active concentration, arousal, cognition, and/or paranoia |
| >40 Hz | Gamma waves | Higher mental activity, perception, problem solving, fear, and consciousness |

Efforts have been made to improve sleep, relieve anxiety, improve learning, and improve cognitive performance by administering binaural beats to people wishing to attain such target mental states.

Holothink, Inc. sells programs that include sound files (e.g., MP3s and CDs) that generate static binaural beats for meditation, stress relief, to increase focus, and aid sleep. However, users of Holothink, Inc. programs become acclimatized to static binaural beats, and thus, these programs can lose their effectiveness with subsequent uses.

In an effort to use binaural beats to induce sleep, Larson et al. (U.S. Pat. Pub. No. 2014/0343354) describe methods comprising an iterative loop of data collection, binaural tone generation/presentation, and analysis of binaural tones. Data collection is accomplished using an accelerometer to detect movement and a sensor to detect brain activity. The data are used to determine a current state of an individual's brain. A microcontroller determines an intermediate brain state between the current brain state and the goal state, and a binaural generator presents binaural tones based on the intermediate brain state to the individual, which influences the individual's brain to change from the current state to the intermediate state. By repeating this process, the individual's brainwaves iteratively approach frequencies associated with sleep. After the individual falls asleep, the system ceases tone delivery. Because the individual's brainwave activity and movement are monitored, the system can detect when the individual is about to awaken prematurely, and can resume presenting tones to maintain the desired sleep state. However, Larson et al. failed to appreciate that individuals become acclimatized to static binaural beats. Thus, when an individual becomes acclimatized to a particular binaural beat, or series of beats, the individual disengages from the presented binaural beat, which diminishes its effectiveness.

U.S. Pat. No. 7,769,439 to Vesely et al. discloses methods and apparatuses to balance, or synchronize, the left and right sides of the brain using binaural beats. When the brainwaves of the left and right hemispheres of the brain are balanced, deep tranquility, flashes of creative insight, euphoria, intensely focused attention, and enhanced learning abilities are reported. Vesley et al. describe apparatuses and methods in which the brainwaves of each hemisphere are measured, and an audio generator generates a binaural beat to compensate for an imbalance in the brainwaves. Contemplated binaural beats can be continuous or intermittent. A feedback mechanism could be provided that ensures proper treatment. Although the brain can learn to balance itself, at least some individuals will acclimatize to the binaural beats, and disengage from treatment. In such cases, individuals typically experience less improvement after each subsequent treatment.

In yet another example that uses a feedback system to vary binaural beats, U.S. Pat. Pub. No. 2013/0177883 to Barnehama et al. attempts to use a feedback system to manipulate a person's brainwaves to improve students' focus and test taking ability. Although the binaural beat provided to the students varies to some degree as a result of the feedback mechanism. Barnehama et al. failed to appreciate that static binaural beats lose effectiveness.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, an object of the inventive subject matter is to provide methods of providing binaural beats that induce target mental states while avoiding acclimatization to the binaural beat provided.

SUMMARY OF THE INVENTION

The following description includes information that may be useful in understanding the present invention. It is not an admission that any of the information provided herein is prior art or relevant to the presently claimed invention, or that any publication specifically or implicitly referenced is prior art.

The inventive subject matter provides methods in which a target mental state is induced in a person using binaural beats having frequencies that change among and within durations. Preferably, the binaural beats are applied irregularly. As used herein, "irregular" binaural frequencies are ones where the time-weighted average slope of the progression over the entire period of time varies by more than 10%, where each time-weighted average comprises at least 10 seconds, and preferably comprises at least 30 seconds, at least 2 minutes, or at least 5 minutes. In one aspect of the inventive subject matter, a stressed person having a base binaural beat can be induced to assume a relaxed mental state having a target binaural beat. In another aspect of the inventive subject matter, a distracted or unfocused person having a base binaural beat can be induced to assume a focused mental state having a target binaural beat. In yet other aspects of the inventive subject matter a fearful person having a base binaural beat can be induced to assume a warrior mental state having a target binaural beat. In further aspects of the inventive subject matter, an awake person having a base binaural beat can be induced to assume a sleep mental state having a target binaural beat. Binaural beats having frequencies that are not consistent or do not change at an easily predictable rate engage the person, prevent the person from becoming acclimatized to the binaural beats, and therefore, have an increased effectiveness over the course of one or more treatments.

Contemplated methods of inducing a target mental state in a person include a step of providing a system that administers binaural beats to the person at varying frequencies. The binaural beats are administered over the course of multiple durations, but preferably at least three durations. During a first duration, binaural beats are administered according to a first progression of frequencies within a first range. During a subsequent second duration, the binaural beats are administered according to a second progression of frequencies within a second range. During a subsequent third duration, binaural beats are administered according to a third progression of frequencies within a third range. During at least the first and third durations, the progression of frequencies advance from the base binaural beat towards the target binaural beat. As used herein, progressions from a base binaural beat towards a target binaural beat do not necessarily comprise the base binaural beat and target binaural beats themselves, but rather have a progression that comprises a path from the base to the target.

It should be appreciated that the inventive methods can further comprise, fourth, fifth, sixth, seventh, eighth, ninth, tenth, eleventh, twelfth, thirteenth, fourteenth, fifteenth, sixteenth, seventeenth, eighteenth, nineteenth, twentieth, or an even greater number of durations during which the system is configured to administer binaural beats to a person in a progression of frequencies within a range.

A time-weighted average of the first progression is greater than a time-weighted average of the second progression, and a time-weighted average of the second progression after the first progression is generally less than a time-weighted average of the third progression. Preferably, progressions in which the frequency of the binaural beats are alternatively increased and/or decrease over the course of each progressive duration, preventing the person from getting used to or becoming immune to the binaural beats. Durations can be continuous, or there can be periods of silence and/or absence of binaural beat administration between durations. In some embodiments, the system could randomize the time-weighted average, or could vary the time-weighted average in accordance with a pre-set algorithm, for example increasing the binaural frequency by 1 Hz every 30 seconds for 3 minutes, decreasing the binaural frequency by 0.25 Hz every 30 seconds for 2 minutes, and then increasing the binaural frequency by 1.5 Hz every 30 seconds for 4 minutes. In another embodiment, the system could increase the binaural frequency by 1 Hz every 30 seconds for 3 minutes, increase the binaural frequency by 0.25 Hz every 30 seconds for 2 minutes, and then increase the binaural frequency by 1 Hz every 30 seconds until the target binaural frequency is reached.

Preferred progressions are preferably pre-established, although a dynamic modification of progressions (e.g. as a function of a randomizer or as a feedback mechanism) are also contemplated. Progressions could be selectable by the user or a treatment provider. Progressions can also be customizable, wherein one or more of the frequency progressions, the amplitudes, and the pitches of the auditory stimuli delivered to each ear can be selected. Dynamic progressions that change in response to biofeedback, a lighting condition, a tactile condition, or other environmental conditions can be used. For example, the system could have an electroencephalogram that detects a wave pattern of the person's brain, and as the wave pattern increases or decreases in frequency over a time-weighted average duration (e.g. 0.5 seconds or 1 second), the rate at which the binaural frequency could also be altered accordingly. Regardless of whether or not the binaural beat frequency is pre-established, when the binaural beats are administered to the person, the frequencies of the binaural beats during the different durations engage the person since the time-weighted average change during each duration is different from one another and prevent the person from becoming acclimatized to the binaural beats, and therefore, maintain effectiveness over the course of one or more treatments.

The inventive methods can optionally utilize filtering and/or gating of an audio file to produce at least one of the first, second and third progressions of frequencies.

To augment the person's experience, music can be administered to the person (self-administered or otherwise) during at least one of the first, second, and third durations. Another option is to administer at least one of rain sounds, ocean wave sounds, and wind sounds to the person during at least one of the first, second, and third durations.

Including a further step of administering an electrical stimulus to the person during at least one of the first, second, and third durations enhances the effects of administering binaural beats having changing frequencies. That is, administering binaural beats having changing frequencies in combination with an electrical stimulus enhances engagement of the person, enhances the effect of preventing the person from becoming acclimatized to the binaural beats, and further sustains the effectiveness of the inventive methods over the course of one or more treatments.

Administering a visual stimulus, administering a tactile stimulus, administering an olfactory stimulus, and/or administering a neurotransmitter and/or a neurotransmitter precursor to the person during any one of the durations enhances the process.

In another embodiment, a method of inhibiting a person from acclimatizing to a binaural beat comprises: (1) generating a first frequency pattern; (2) superimposing a second frequency pattern on the first frequency pattern; (3) generating a binaural beat according to the second frequency pattern; and (4) administering the binaural beat to the person.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 3 shows a person wearing a device system that applies the binaural beats utilizing the inventive patterns disclosed herein.

FIG. 4 shows a person lying in bed with speakers coupled to a computer system which applies biaural beats to the person.

DETAILED DESCRIPTION

Figure 1:
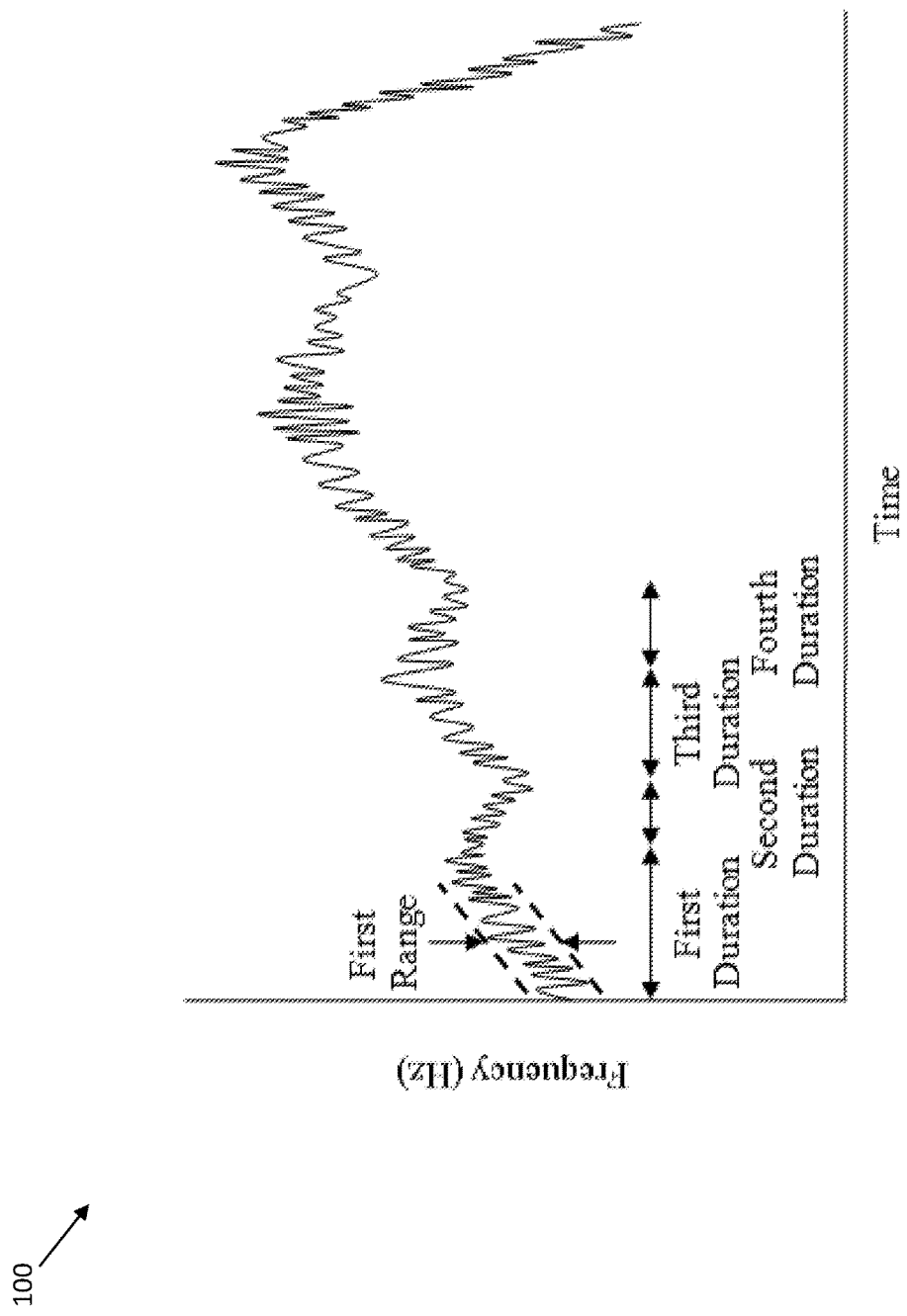
FIG. 1 is a time v. frequency plot for binaural beats administered by a system in which the binaural beat increases from the beginning to the end of a multi-duration session.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be noted that any language directed to a computer system should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network. Computer software that is "programmed" with instructions is developed, compiled, and saved to a computer-readable non-transitory medium specifically to accomplish the tasks and functions set forth by the disclosure when executed by a computer processor.

Binaural beats are perceived when two auditory stimuli of different frequencies are presented to each ear. The frequency of the binaural beat is equal to the difference between the frequencies applied to each ear. Although people generally perceive auditory stimuli having frequencies ranging from 20 Hz to 20 k Hz, the brain perceives binaural beats having frequencies below 20 Hz. In some cases, the listener's brainwaves can synchronize with, or become entrained, with the administered binaural beat. Binaural beat entrainment of brainwaves can be detected using electroencephalography.

To administer binaural beats auditory stimuli within the perceptible frequency range, 20 Hz to 20 k Hz, more typically between 200 Hz and 400 Hz, are administered to each ear. The binaural beat is only perceived with the auditory stimuli are each delivered to only one ear. In other words, no perception or entrainment has been observed when both auditory stimuli are provided to the listener's ambient environment.

The volume of each auditory stimulus is also typically within the audible range. For example, 2 kHz sounds are audible to nearly 0 dB, 10 kHz sounds are audible at 20 dB and greater volumes, and 100 Hz sounds are audible 40 dB and above.

Acclimatization to binaural beats can be avoided by varying the frequency of binaural beats to keep an entity receiving the binaural beats engaged (e.g. an animal such as a person). Such binaural beats maintain the ability to entrain the person's brainwaves each time they are administered to the person, from a base frequency associated with a base mental state to a target frequency associated with a target mental state. This is in contrast to decreases in effectiveness that have been reported when other, more regular or predictable methods are used.

The inventive methods induce a target mental state in a person using binaural beats having irregular frequencies. As shown in Table 1, target mental states are associated with brainwave frequencies. For example, to induce sleep in persons experiencing insomnia, the persons' brainwaves could be trained from a base waking state (e.g., beta brainwaves having frequencies between 13 Hz and 39 Hz) to a target sleep state (e.g., alpha brainwaves having frequencies between 7 Hz and 13 Hz, theta brainwaves having frequencies between 4 Hz and 7 Hz, and delta brainwaves having frequencies less than 4 Hz).

A person experiencing a stressed base mental state (e.g., exhibiting brainwave frequencies above 13 Hz) can be induced to assume a relaxed target mental state (e.g., 7-13 Hz) by administering binaural beat frequencies closer to the target mental state. To improve focus and/or performance on cognitive tasks (e.g., tests, problem solving, etc.), a person's brainwaves can be trained to between 13 Hz and 39 Hz by administering binaural beat frequencies closer to the target mental state. To induce a warrior mental target state, the inventive methods train the person's brainwaves to greater than 40 Hz by administering binaural beat frequencies closer to the target mental state. Preferably, the administered binaural beat frequencies are not applied in a regular linear fashion from a base binaural beat to a target binaural beat, but are applied in an irregular manner to prevent the person from building a resistance to the brainwave training.

The methods of inducing a target mental state in a person include a step of providing a system that administers binaural beats to the person at varying frequencies. The binaural beats are administered over the course of many durations, but generally at least three durations.

Figure 2:
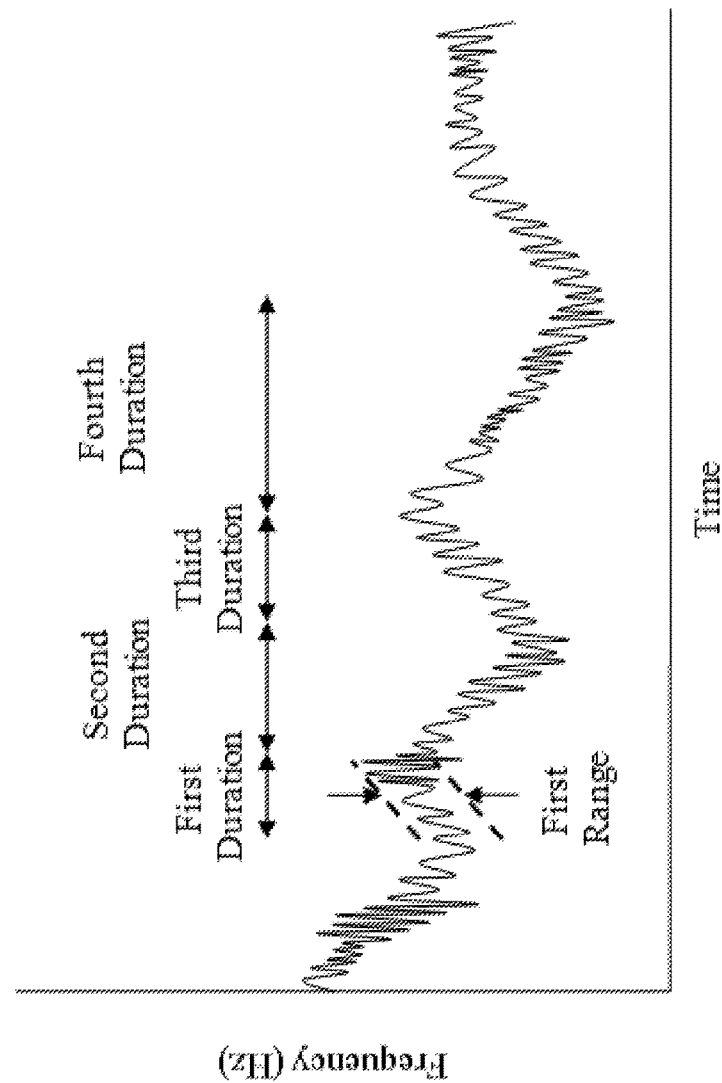
FIG. 2 is a time v. frequency plot for binaural beats in which the binaural beat decreases from the beginning to the end of a multi-duration session.

Exemplary binaural beat frequency progressions are shown in FIGS. 1 and 2. The frequency progressions shown follow a dual oscillation that resembles a variable, high frequency, low amplitude wave function summed with a variable, low frequency, high amplitude wave function. Preferably, the period and amplitude of the frequencies in each progression vary, although constant period and amplitude time v. frequency functions are not excluded.

As shown in FIG. 1, during a first duration, a first progression of binaural beat frequencies oscillates within a first range. Although a binaural beat frequency during the first duration can fall below the frequency at the beginning of the first duration (initial frequency), the time-weighted average of the oscillations increases to a frequency that is higher than the initial frequency. As used herein, the "range" of frequencies utilized within a duration is defined to exclude frequencies greater than 50 Hz, and volumes to the person less than 40 dB. And similarly, "time-weighted averages" are calculated by only excluding binaural beats having frequencies greater than 50 Hz, and volumes to the person less than 40 dB.

During a subsequent second duration, the binaural beats are administered according to a second progression of frequencies within a second range. As shown in FIG. 1, a time weighted average of a high frequency oscillation within the second range (not labeled) generally decreases from the beginning of the second duration to a frequency that is lower than the frequency at the beginning of the second duration.

During a subsequent third duration, binaural beats are administered according to a third progression of frequencies within a third range (not labeled). Thus, it should be appreciated that, a time-weighted average of the first progression is higher than a time-weighted average of the second progression, and a time-weighted average of the second progression is lower than a time-weighted average of the third progression. The inventive methods can further comprise, fourth, fifth, sixth, seventh, eighth, ninth, tenth, eleventh, twelfth, thirteenth, fourteenth, fifteenth, sixteenth, seventeenth, eighteenth, nineteenth, twentieth, or an even greater number of durations during which the system is configured to administer binaural beats to a person in a progression of frequencies within a range.

During each of the three durations, the way the frequencies vary within the respective ranges can be pre-determined, can be random or pseudo random, or can be established as a function of one or more body or ambient conditions.

In FIG. 2, binaural beat frequencies for decreasing persons' brainwave frequencies are shown. In this situation as well, progressions in which the average frequency of the binaural beats alternatively increase and/or decrease over the course of each duration are contemplated.

In both FIGS. 1 and 2, durations can be continuous, or there can be periods of silence and/or absence of binaural beat administration between durations.

Pre-established progressions are generally preferred because they are easier to implement than methods that require sensors and biofeedback, and because experimentation has demonstrated that even pre-established progressions can be sufficient to keep the person engaged with the binaural beats. However, progressions can be customized, wherein one or more of the frequency progressions, the amplitudes, and the pitches of the auditory stimuli delivered to each ear can be selected. For example, a person can require less time for their brain to be entrained with a particular binaural beat, in such cases one or more progressions can be shortened.

Progressions can also be selected by the person receiving the binaural beats, or by another entity, as for example a treatment provider. For example, systems can include a graphical user interface. Alternatively, buttons or knobs can be used to select desired mental states. Systems can include cell phones, phablets, tablets, laptop computers, iPods™, or other mp3™ players in which a person can select an audio file that includes auditory stimuli. When the person listens to the audio file, the person perceives the binaural beat administered by the system.

The system could also administer dynamic binaural beat progressions that change in response to biofeedback, a lighting condition, a tactile condition, or other environmental conditions can be used. For example, a system can change the target mental state from a sleep state to a waking state when morning light and/or a minimum ambient temperature are detected. Advantageously, the frequencies of the binaural beats during the first, second and third durations engage the person, prevent the person from becoming acclimatized to the binaural beats, and therefore, maintain effectiveness over the course of one or more treatments.

Preferably, the first range is between 10 Hz and 15 Hz, inclusive. The second range is between 8 Hz and 12 Hz, inclusive. The third range is between 10 Hz and 16 Hz, inclusive. The inventive subject matter further includes first ranges in which the frequencies of the binaural beats can range between 0 Hz and 2 Hz, 2 Hz and 4 Hz, 4 Hz and 6 Hz, 6 Hz and 7 Hz, 7 Hz and 9 Hz, 9 Hz and 11 Hz, 11 Hz and 13 Hz, 13 Hz and 15 Hz, 15 Hz and 17 Hz, 17 Hz and 19 Hz, 19 Hz and 20 Hz, 20 Hz and 22 Hz, 22 Hz and 24 Hz, 24 Hz and 26 Hz, 26 Hz and 28 Hz, 28 Hz and 30 Hz, 30 Hz and 32 Hz, 32 Hz and 34 Hz, 34 Hz and 36 Hz, 36 Hz and 38 Hz, 38 Hz and 40 Hz, 40 Hz and 42 Hz, 42 Hz and 44 Hz, 44 Hz and 46 Hz, 46 Hz and 48 Hz, and between 48 Hz and 50 Hz, inclusive.

In further regard to ranges, outlier binaural beats produced by a system can be removed, for example by filtration or grating. Exemplary methods of filtration and grating have been described by Dr. Tomatis and his successors. In one example of contemplated filtration methods, specific frequencies are removed from an existing sound recording and are processed to removed and reintroduced at will. On the other hand, a grating could be used to generate a random sonic event, such as a jump from a high to a low frequency. Such random sonic events exercise the muscles of the middle ear thereby engaging the person.

It is further contemplated a person's engagement/brainwave entrainment could be enhanced by incorporating at least five peak frequencies within at least one of the durations. Further engagement can be attained by the person when at least one of the binaural beats during the first duration has a frequency that is at least 15% higher than a high end of the first range. For example, when the binaural beat frequencies near the end of the first range are greater than the binaural beat frequencies near the beginning of the first range, and at least one of the binaural beats during the first duration is at least 15% higher than a high frequency of the binaural beats near the end of the first range, greater engagement of the person's brainwaves can be observed. In another example, when the binaural beat frequencies near the beginning of the first range are greater than the binaural beat frequencies near the end of the first range, and at least one of the binaural beats during the first duration is at least 15% higher than a high frequency of the binaural beats near the beginning of the first range, greater engagement of the person's brainwaves can be observed.

Preferably, at least one of the first, second and third durations spans 1.5 to 3 minutes. However, other durations are contemplated, as for example, at least one of the first, second and third durations spanning 2 to 5 minutes. It is also preferred that at least one pairing of the first, second and third durations differ by at least 3 minutes. Moreover, contemplated lengths of all pairings of the first, second and third durations differ by at least 2 minutes.

In regard to the auditory stimuli that produce perception of the binaural beats, contemplated methods can further comprise a step of configuring the system to produce at least some of the binaural beats of the first progression by rendering auditory stimuli having different first and second pitches at between 100 Hz and 200 Hz, inclusive. Advantageously, auditory stimuli within this range result in strong brainwave entrainment. Entrainment can be stronger in some persons when 100 Hz and 200 Hz auditory stimuli are administered than when higher frequency auditory stimuli are used. Auditory stimuli preferably have frequencies between 20 Hz and 100 Hz, 200 Hz and 300 Hz, 300 Hz and 400 Hz, 400 Hz and 500 Hz, 500 Hz and 600 Hz, 700 Hz and 800 Hz, 800 Hz and 1000 Hz, 1000 Hz and 2000 Hz, 2000 Hz and 3000 Hz, 3000 Hz and 4000 Hz, and 4000 Hz and 5000 Hz, inclusive. In one aspect of the inventive subject matter, the frequencies of the auditory stimuli start from outside the range between 100 Hz and 200 Hz to within the range between 100 Hz and 200 Hz during at least a portion of a session.

Tactilely perceptible vibrations and visual frequencies within the range of 100 Hz and 200 Hz can further enhance brainwave entrainment. As such, tactilely perceptible vibrations and/or visual frequencies could also be administered to a person either in addition to, or alternatively to, the auditory stimuli.

To further engage the person, the amplitudes of audio stimuli administered to each ear of the person can change within and/or among durations. Amplitude changes can be time-volume weighted. For example, methods according to the inventive subject matter can further comprise a step of configuring the system to vary the auditory stimuli that give rise to the binaural beats of the first progression by at least 10 dB over the course of a given duration. The amplitudes selected should be audible and comfortable for the person to perceive. The audio stimuli are preferably administered between 20 dB and 40 dB, 40 dB and 60 dB, 60 dB and 80 dB, 80 dB and 110 dB, inclusive. Thus, the volume can be adjusted for persons with sensitive hearing, with hearing within a normal range, and with impaired hearing.

Because the auditory stimuli used to administer binaural beats can be displeasing, music can be co-administered to the person during at least one of the first, second, and third durations. Another option is to co-administer at least one of rain sounds, ocean wave sounds, and wind sounds to the person. Other sounds such as rainforest sounds, or synthetic tones can also be co-administered with the auditory stimuli that give rise to the perception of binaural beats. Yet another option is to utilize frequencies within the music or other sound files to generate the binaural beat. For example, a piano concert in which middle C is not played at 256 Hz, but is played at 250 Hz to the right hear, and is played at 262 Hz to the left ear.

Preferably, the system automatically audits and administers music from any genre to create suitable track to play for the person. This is preferably performed automatically by software of the system to create a personalized neuroacoustic track that meets the ever-changing needs of a person. Preferably, the system has specific mental states or binaural frequencies that are associated with musical tracks, such that where a person selects a target mental state (associated with a binaural frequency) or a target binaural frequency itself, that musical track is played. In other embodiments, the binaural frequency that the system applies to the person is used to select a musical track. For example, where the system first applies a binaural frequency associated with a stressed state, the system could select music associated with a stressed state, and then the system applies a binaural frequency associated with a calm state, the system could select music associated with a calm state. The system could be configured to periodically poll the binaural frequency applied, or could simply poll the binaural frequency at the end of each musical sample, or near the end of each musical sample (e.g. 10 seconds or 20 seconds before the end of the song). Other samples, such as light samples (e.g. movies/shows/colors/screensavers) or tactile samples (rates of vibration) could be used in addition to, or as an alternative to, musical samples.

Including a further step of administering an electrical stimulus to the person during any of the durations, or preferably each of the durations, enhances the effects of administering binaural beats having changing frequencies. The electrical stimulus can have a frequency that matches that of the binaural beat administered. Alternatively, the electrical stimulus can be static or intermittent. The electrical stimulus can also follow a square or sinusoidal wave form. The electrical stimulus can also be administered in a random or otherwise attention grabbing manner. As such, administering binaural beats having changing frequencies in combination with an electrical stimulus can enhance engagement of the person, can enhance the effect of preventing the person from becoming acclimatized to the binaural beats, and can further sustain the effectiveness of the inventive methods over the course of one or more treatments.

Administering a visual stimulus, administering a tactile stimulus, administering an olfactory stimulus, and/or administering a neurotransmitter and/or a neurotransmitter precursor to the person during at least one of durations could also speed up the time within which the person achieves the target mental state. Visual stimuli can include visual displays such as LED lights (monochromatic, white, or colored), visual patterns (e.g., cloud formations or bodies of water), films, virtual reality environments etc. Tactile stimulus can include massage, sensory deprivation environments, water baths, heat/cooling pads, and others. Olfactory stimuli can be administered in the form of topical essential oils, teas, essential oil diffusers, incense, fresh flowers and/or herbs or other means.

Thus, methods of inhibiting a person from acclimatizing to a binaural beat can comprise: (1) generating a first frequency pattern; (2) superimposing a second frequency pattern on the first frequency pattern; (3) generating a binaural beat according to the second frequency pattern; and (4) administering the binaural beat to the person. For example, in FIG. 1, the first frequency pattern comprises the low frequency, upward oscillation, and the second frequency pattern comprises the higher frequency oscillation pattern having a generally narrower amplitude range than the first frequency pattern. FIG. 2 shows a first frequency pattern having a low frequency and a generally downward trend. The second frequency pattern comprises higher frequencies and a lower amplitude range than the first frequency pattern. The frequency patterns shown in FIGS. 1 and 2 should be viewed as non-exclusive, and other frequency patterns, which can be used to induce a person to assume a desired mental state without becoming acclimatized to the binaural beats, could be utilized so long as the frequency pattern as whole administers from a base binaural beat to a target binaural beat.

Preferably, the first range (i.e., the ranges of frequencies used within the first duration) is between 10 Hz and 15 Hz, inclusive. Unless the context dictates the contrary, all ranges set forth herein should be interpreted as being inclusive of their endpoints and open-ended ranges should be interpreted to exclude commercially impractical values. Similarly, all lists of values should be considered as inclusive of intermediate values unless the context or further definition indicates the contrary. The second range is preferably between 8 Hz and 12 Hz, inclusive. The third range is preferably between 10 Hz and 16 Hz, inclusive. The inventive subject matter further includes ranges in which the frequencies of the binaural beats can range between 0.05 Hz and 4 Hz, 4 Hz and 7 Hz, 7 Hz and 13 Hz, 13 Hz and 20 Hz, 20 Hz and 30 Hz, and between 30 Hz and 40 Hz, inclusive.

To achieve the goal of continued engagement of the brain of the person, the first progression of frequencies preferably includes at least five peak frequencies. And more preferably, each of the first, second and third progressions of frequencies includes at least five peak frequencies. Further engagement can be attained by the person when at least one of the binaural beats during the first duration has a frequency that is at least 15% higher than a high end of the first range. For example, when the binaural beat frequencies at the end of the first range are greater than the binaural beat frequencies at the beginning of the first range, and at least one of the binaural beats during the first duration is at least 15% higher than a high frequency of the binaural beats at the end of the first range, greater engagement of the person's brainwaves can be observed. In another example, when the binaural beat frequencies at the beginning of the first range are greater than the binaural beat frequencies at the end of the first range, and at least one of the binaural beats during the first duration is at least 15% higher than a high frequency of the binaural beats at the beginning of the first range, greater engagement of the person's brainwaves can be observed.

With respect to contemplated durations, at least one of the first, second and third durations spans 1.5 to 3 minutes, inclusive. At least one of the first, second and third durations span 2 to 5 minutes, inclusive. Typically, at least one pairing of the first, second and third durations differ by at least 3 minutes. Moreover, contemplated lengths of all pairings of the first, second and third durations differ by at least 2 minutes.

In regard to the auditory stimuli, methods according to the inventive subject matter can further comprise a step of configuring the system to produce at least some of the binaural beats of the first progression by rendering auditory stimuli having different first and second pitches at between 100 Hz and 200 Hz, inclusive. Advantageously, auditory stimuli within this range tend to have a higher efficacy in test subjects than auditory stimuli outside this range.

To further engage the person, the amplitudes of audio stimuli administered to each ear of the person can change. Amplitude changes can be time-volume weighted. For example, methods according to the inventive subject matter can further comprise a step of configuring the system to vary the amplitudes of the audio stimuli that generate perception of the binaural beats of a given progression by at least 10 dB over the course of the corresponding duration.

Thus, one having ordinary skill in the art appreciates that the system can further include a selector configured to adjust the target mental state characterized by among at least alpha brainwaves, beta brainwaves, gamma brainwaves and delta brainwaves.

FIG. 3 shows an exemplary system 300 used to administer the different progressions of binaural beat frequencies to a person 310. Here, person 310 is wearing a wearable device 320 having audio speakers 321 that together administer binaural beat frequencies to the person. Preferably, wearable device 320 is controlled wirelessly via computer system 330, such as a mobile phone controlling wearable device 320 via Bluetooth, or a centralized computer controlling device 320 via wifi. In other embodiments, device 320 could have an embedded processor, memory, and a user interface that allows a user to provide commands to device 320, such as a microphone that receives audio commands.

Wearable device 320 could also have an optional electroencephalogram 324 that is used to detect the current brain wave state of the person to provide a feedback mechanism to the system, allowing the system to receive inputs regarding whether the person is reacting positively to the treatment. Wearable device 320 could also have one or more optional non-binaural transmitter 322 that administers non-binaural signals to the person, such as other audio signals (e.g. music, rain sounds, ocean wave sounds, and wind sounds), electrical stimuli, visual stimuli, tactile stimuli, or even olfactory stimuli. The other signals are preferably applied as a function of the concurrently-administered binaural beat frequency. For example a tactile vibration applied preferably shares the same frequency as the binaural beat (or is 1 or 2 Hz greater or less than the binaural beat), or a flashing light stimuli preferably shares the same frequency as the binaural beat (or is 1 or 2 Hz greater or less than the binaural beat).

FIG. 4 shows another exemplary system used to administer the different progressions of binaural beat frequencies to a person 410. Here, person 410 is lying in bed and cannot wear a device, so speakers 421 and 422 are coupled to computer system 420, which applies binaural beats to person 410, and non-binaural transmitter 423 could optionally be used to simultaneously deliver non-binaural signals to person 410. While non-binaural transmitter 423 is shown as a lightbulb, any other non-binaural transmitters could be used, for example vibration motors (e.g. coupled to the bed of person 410), an aromatherapy machine, a separate speaker, or a movie display or projector.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention can contain certain errors necessarily resulting from the standard deviation found in their respective testing measurements.

What is claimed is:

1. A method of inducing a target mental state in a person comprising:
   receiving a base binaural beat at the person;
   receiving a target binaural beat at the person;
   administering a first progression of binaural beat frequencies from the base binaural beat to the target binaural beat within a first range to the person during a first duration;
   administering a second progression of binaural beat frequencies within a second range to the person during a second duration after the first duration; and
   administering a third progression of binaural beat frequencies from the base binaural beat to the target binaural beat within a third range to the person during a third duration after the second duration,
   wherein a time-weighted average of the first progression is greater than a time-weighted average of the second progression, and a time-weighted average of the second progression is less than a time-weighted average of the third progression.

2. The method of claim 1, wherein the second progression of binaural beat frequencies progresses from the target binaural beat to the base binaural beat.

3. The method of claim 1, wherein the second progression of binaural beat frequencies progresses from the base binaural beat to the target binaural beat at a time-weighted average less than both the time-weighted average of the first progression and the time-weighted average of the third progression.

4. The method of claim 1, wherein the time-weighted average of the third progression is greater than the time-weighted average of the first progression.

5. The method of claim 1, wherein the first range is between 10 Hz and 15 Hz, inclusive, the second range is between 8 Hz and 12 Hz, inclusive, and the third range is between 10 Hz and 16 Hz, inclusive.

6. The method of claim 1, wherein the first progression of frequencies comprises at least five peak frequencies.

7. The method of claim 1, wherein each of the first, second and third progressions of frequencies comprises at least five peak frequencies.

8. The method of claim 1, wherein at least one of the first, second and third durations span 1.5 to 3 minutes, inclusive.

9. The method of claim 1, wherein lengths of at least one pairing of the first, second and third durations differ by at least 3 minutes.

10. The method of claim 1, wherein lengths of all pairings of the first, second and third durations differ by at least 2 minutes.

11. The method of claim 1, wherein the first progression comprises different first and second pitches at between 100 Hz and 200 Hz, inclusive.

12. The method of claim 1, wherein the first progression comprises varying binaural beats of at least 10 dB.

13. The method of claim 1, wherein the step of receiving the target binaural beat at the person comprises receiving a selection of at least an alpha state, a beta state, a gamma state and a delta state.

14. The method of claim 1, wherein at least one of the first, second, and third progressions of frequencies is administered via at least one of filtering and gating an audio file.

15. The method of claim 1, further comprising also administering a non-binaural audio sample to the person during at least one of the first, second, and third durations.

16. The method of claim 15, wherein the non-binaural audio sample comprises at least one of music, rain sounds, ocean wave sounds, and wind sounds.

17. The method of claim 1, further comprising also administering a non-binaural stimulus to the person during at least one of the first, second, and third durations, wherein the non-binaural stimulus comprises at least one of (a) an electrical stimulus, (b) a visual stimulus, (c) a tactile stimulus, and (d) an olfactory stimulus.

18. The method of claim 17, wherein the non-binaural stimulus is applied as a function of the concurrently-administered binaural beat frequency.

19. The method of claim 1, further comprising administering at least one of a neurotransmitter and a neurotransmitter precursor prior to the third duration.

* * * * *